United States Patent [19]

Jovanovics et al.

[11] 4,209,443

[45] Jun. 24, 1980

[54] PROCESS FOR SEPARATING PHARMACEUTICALLY ACTIVE DIINDOLE ALKALOIDS

[75] Inventors: Karola Jovánovics; Lajos Dancsi; Sándor Eckhardt; Csaba Lörincz; János Sugár; Zsuzsa Relle née Somfai; Kálmán Szasz; József Tamas; Aron Szöllösy, all of Budapest, Hungary

[73] Assignee: Richter Gedeon Vegyeszeti Gyar Rt., Budapest, Hungary

[21] Appl. No.: 882,418

[22] Filed: Mar. 1, 1978

Related U.S. Application Data

[63] Continuation-in-part of Ser. No. 762,235, Feb. 13, 1976, abandoned.

[30] Foreign Application Priority Data

Feb. 13, 1976 [HU] Hungary ............................... RI 585

[51] Int. Cl.² .......................................... C07D 519/04
[52] U.S. Cl. ................................... 260/244.4; 424/258
[58] Field of Search .......................... 260/287 B, 244.4

[56] References Cited

U.S. PATENT DOCUMENTS

| 3,392,173 | 7/1968 | Hargrove .......................... 260/287 B |
| 3,954,773 | 5/1976 | Neuss et al. ...................... 260/286 R |
| 3,968,113 | 7/1976 | Neuss et al. ...................... 260/287 B |

OTHER PUBLICATIONS

Brown et al., Quantitative Chemistry, p. 457, (1964).

*Primary Examiner*—David Wheeler
*Attorney, Agent, or Firm*—Karl F. Ross

[57] ABSTRACT

A mixture of minor diindole alkaloids from Vinca-containing vinblastine and 4-deacetoxy-vinblastine vines, are separated by subjecting the mixture to a deacetylation to correct the vinblastine to deacetyl-vinblastine prior to chromatographic separation of said mixture in a single stage.

2 Claims, No Drawings

PROCESS FOR SEPARATING PHARMACEUTICALLY ACTIVE DIINDOLE ALKALOIDS

CROSS-REFERENCE TO RELATED APPLICATION

This is a continuation-in-part application of Ser. No. 762,235 filed Feb. 13, 1976 now abandoned.

FIELD OF THE INVENTION

This invention relates to a process for preparing a pharmaceutically active diindole alkaloid or acid-addition salts thereof. Furthermore, the invention relates to a process for preparing pharmaceutical compositions containing such compounds as active principles. More specifically, the invention relates to a process for preparing 4-deacetoxy-vinblastine, a minor alkaloid of Vinca rosea L., or its acid-addition salts.

BACKGROUND OF THE INVENTION

As is known, the minor alkaloids of Vinca rosea L. with diindole skeletons possess valuable cytostatic effects (U.S. Pat. Nos. 3,097,137 and 3,205,22; Hungarian Patent specifications Nos. 153,200; 154,715 and 160,967.) Of these minor alkaloids, vincristine is the one regarded to be the most valuable, making up some hundredths of a percent of the total alkaloid content, whereas the less effective vinblastine and vinleurosine are present in an amount of about 1 to 2 percent of the total alkaloid content.

In the recent past, the demand for the latter two alkaloids has increased considerably, which can be attributed to the recognitions that vinblastine can be converted into the more valuable vincristine by a semisynthetic process (Hungarian Patent specification No. 165,599), and that the N-formyl derivative of vinleurosine (Hungarian Patent specification No. 165,986) also inhibits the growth of tumors resistant towards the cytostatic agents known before.

The more recent investigations in this field have been directed to the preparation of further effective semisynthetic alkaloid derivatives, such as the carboxamide and deacetyl derivatives (published German patent applications Nos. 1,795,763 and 2,415,890), as well as on the isolation of further minor alkaloids, such as vincadioline, leurocolombine (U.S. Patent Nos. 3,887,565 and 3,890,325) and 4-deacetoxy-vinblastine [N. Neuss, A. J. Barnes and L. L. Huckstep: Experimentia 31/1, (18–19)].

The isolation of the further minor alkaloids was rendered possible by the improvements in chromatographic techniques, more particularly, by the use of high-pressure chromatographs. Using such equipment, even compounds with rather similar physical constants, such as the retention factor—$R_f$, and chemical structures can be separated successfully from each other. Nowadays high-pressure chromatographs can be applied successfully for laboratory scale operations; their utilization is, however, extremely complicated and expensive in large-scale techniques.

N. Neuss et al. [Experimentia 31/1, 18–19(1975)] succeeded in isolating 4-deacetoxy-vinblastine, an accompanying alkaloid of vinblastine not known before, by subjecting vinblastine to two chromatographical separations and two recrystallizations. The U.V. and I.R. spectra of vinblastine and 4-deacetoxy-vinblastine are very closely related, and the difference between their retention factors $R_f$ amounts to only 0.03. In the cited publication, the authors described the separation technique for the two alkaloids and the difficulties, which had arisen in connection with their structure determinations. They did not give, however, any information on the pharmacological or other properties or effects of the new alkaloid.

THE INVENTION

This invention is based on the recognition that 4-deacetoxy-vinblastine has surprising pharmacological advantages over vinblastine and other diindole alkaloids having anti-tumor activity; thus the invention provides a new entity useful in the therapy of malignant tumors, which comprises 4-deacetoxy-vinblastine as active material. The invention also provides a new process for the preparation in high yield and purity of 4-deacetoxy-vinblastine, acid addition salts thereof.

In the process of the invention an enriched mixture of the sulfate salts of minor diindole alkaloids is used as the starting substance. This enriched mixture is isolated from the plant (Vinca rosea L.) according to the method described in Hungarian Pat. No. 160,967.

According to the newly developed method, the enriched alkaloid salt mixture is processed as follows:

An alkanolic solution of the alkaloid salt mixture is treated with an organic base to liberate the alkaloid bases. The vinleurosine base, which separated from the reaction mixture, is filtered off, and the filtrate is evaporated under reduced pressure. The residue is dissolved in an organic solvent, in which the salt of the organic base applied to liberate the alkaloid base is separated. The separated by-product is filtered off. The filtrate is extracted with an aqueous phosphate buffer solution (pH=3.7 to 4.3). The aqueous-acidic extract is acidified to pH 3.7 to 4.1 with phosphoric acid, and then the acidic solution is extracted with a chlorinated hydrocarbon. The major portion of vinblastine is then isolated from this chlorinated hydrocarbon phase, and the aqueous-acidic phase was subjected to further workup.

It has been found that upon the above treatment the accompanying alkaloids of vinblastine are enriched in the aqueous-acidic phase.

Furthermore, it has been found that, besides the already known vincristine, N-demethyl-vinblastine and minor amounts of residual vinblastine, a fourth alkaloid, 4-deacetoxy-vinblastine, can also be detected in the mixture of the accompanying alkaloids.

Upon examining the separation possibilities of the four alkaloids it has been found that when this alkaloid mixture from the aqueous phase is formylated to convert N-demethyl-vinblastine, (a substance difficult to separate from vinblastine), into vincristine, the resulting alkaloid mixture, now containing only the remaining three components, can be separated easily to the individual components by subjecting it to simple extraction procedures and chromatography performed on a conventional column chromatograph.

This major separation of the vinblastine, 4-deacetoxy-vinblastine and vincristine by extraction and chromatography can be performed directly thus providing a first set of eluted fractions containing 4-deacetoxy-vinblastine; a second set of fractions containing a mixture of about equal parts of 4-deacetoxy-vinblastine and vinblastine; a third fraction containing vinblastine and a residual of vincristine.

The second fraction (supra) containing the mixture 4-deacetoxy-vinblastine and vinblastine may be further chromatographed as described in Ser. No. 762,235. Of each 0.6 gm of alkaloid in the second fraction approximately 0.4 gm of the two components can be isolated by this second chromatographic separation.

However, we have discovered an alternate method for the separation of mixtures containing vinblastine and 4-deacetoxy-vinblastine. This method, which involves a deacetylation treatment with either strong acid or alkali carbonate, converts the vinblastine in the mixture to deacetylvinblastine.

Thus the mixture of 4-deacetoxy-vinblastine and vinblastine, having very close retention factors ($R_f$) is converted to a mixture of 4-deacetoxy-vinblastine and deacetyl-vinblastine. The difference in the retention factors between the two latter compounds is greater than that of the original compounds and thus a better separation, in better yield is afforded. Therefore the vinblastine, in deacetylated form, can be more easily separated from the desired 4-deacetoxy-vinblastine.

tine), does not appear at all during the administration of the deacetoxy compound.

The pharmacological tests were performed on transplantable tumors of rats and mice. The effects on L 1210/VS(vinca-sensitive) mouse lymphoid leukemia and L 1210/Ref (vinca-refractory) mouse lymphoid leukemia were tested on $BDF_1$ mice, the effects on Ehrlich ascites carcinomatous tumors and S 37 ascites sarcomatous tumors were examined on Swiss mice, whereas the effects on Novikoff hepatoma were examined on Wistar rats.

The 4-deacetoxy-vinblastine sulfate was dissolved in physiological saline and the solution was administered intraperitoneally into the animals to be tested. In the tests the average prolongation of survival period and the tumor-inhibiting effect were examined in relation to the untreated controls. The results were listed in Table 1. In the Table the symbol T/c represents the ratio of treated animals to the controls, and the term "number of limit-days" means the fourfold of the average survival period observed in the control group.

Table 1

| Tumor | Daily dosage of 4-deacetoxy-vinblastine sulfate mg/kg i.p. | Frequency of treatment | Number of treatments | Average survival period (days) treated | control | T/c × 100 | On the limit-day (days 36 to day 40) lives | tumor-free |
|---|---|---|---|---|---|---|---|---|
| L 1210/VS | 0.9 | once a day | 7 | 11.5 | 8.8 | 128 | 0/6 | 0/6 |
|  | 1.8 | " | 7 | 11.3 | 8.8 | 128 | 0/6 | 0/6 |
|  | 2.0 | " | 16 | 24.5 | 10.3 | 238 | 0/6 | 0/6 |
|  | 4.0 | " | 16 | 27.7 | 10.3 | 269 | 0/6 | 0/6 |
|  | 4.0 | once in every two days | 11 | 27.5 | 10.3 | 267 | 0/6 | 0/6 |
|  | 4.0 | once in every two days | 8 | 17.7 | 8.3 | 213 | 0/6 | 0/6 |
|  | 5.0 | once in every two days | 8 | 20.8 | 8.3 | 251 | 0/6 | 0/6 |
|  | 6.0 | once in every two days | 8 | 24.2 | 8.3 | 291 | 0/6 | 0/6 |
| L 1210/ref | 2.0 | once a day | 7 | 9.5 | 8.0 | 119 | 0/6 | 0/6 |
|  | 4.0 | " | 7 | 11.5 | 8.0 | 144 | 0/6 | 0/6 |
|  | 4.0 | once in every two days | 7 | 11.7 | 8.0 | 146 | 0/6 | 0/6 |
| Ehrlich ascites carcinoma | 3.0 | once a day | 9 | 30 | 17.4 | 174 | 10/10 | 6/10 |
| S 37 ascites sarcoma | 1.8 | once a day | 8 | 68.5 | 18.2 | 376 | 6/8 | 6/8 |
|  | 2.7 | " | 8 | 67.9 | 18.2 | 373 | 7/10 | 7/10 |
| Novikott hepatoma | 0.5 | once a day | 8 | 10.3 | 8.2 | 126 | 0/6 | 0/6 |
|  | 1.0 | " | 8 | 27.7 | 8.2 | 338 | 1/6 | 1/6 |
|  | 1.5 | " | 8 | 24.7 | 7.8 | 317 | 2/6 | 0/6 |
| HK/Ly ascites lymphoma | 2.0 | once a day | 8 | 48.1 | 14.4 | 334 | 0/10 | 0/10 |
|  | 4.0 | " | 8 | 55.0 | 14.4 | 382 | 6/10 | 0/10 |
|  | 6.0 | " | 8 | 47.2 | 14.4 | 328 | 0/10 | 0/10 |

The separated deacetyl-vinblastine can afterwards be reacetylated to vinblastine as a further by-product of this process.

An alternative based upon the above procedure is that after formylation of the alkaloid mixture from which the major part of the vinblastine is removed, the formylated mixture is deacetylated to form the 3-component mixture containing deacetyl-vinblastine, deacetoxy-vinblastine and vincristine. Then chromatography will provide a better separation between the 4-deacetoxy-vinblastine and the deacetyl-vinblastine.

Upon examining the pharmacological properties of 4-deacetoxy-vinblastine sulfate it has been found that the tumor-inhibiting effects of this compound are roughly identical with those of vinblastine, the deacetoxy compound is, however, far less toxic than vinblastine. Neurotoxicity accompanied with paralytic symptoms, a characteristic adverse side-effect of the structurally related compounds (such as vincristine and vinblas- It appears from the table that L 1210/Ref leukemia, resistant towards the known vinca alkaloids, is not sensitive towards 4-deacetoxy-vinblastine, either. On the other hand, a significant dosage-dependent inhibiting effect can be observed for all the other transplanted tumors, said inhibiting effect being the most intensive for Novikoff hepatoma. When administering 4-deacetoxy-vinblastine sulfate into rats or mice in daily dosages of 1 to 10 mg/kg, preferably 1 to 6 mg/kg, the survival period increases by about 50 to 250 percent.

In the human therapy, intravenous or infusion methods of administration are recommended. The compound can be administered in daily dosages of 0.1 to 0.5 mg/kg.

The toxicity data of 4-deacetoxy-vinblastine, compared to those of other known vinca alkaloids, are listed in Table 2.

Table 2

| Compound | LD$_{50}$ mg/kg |
| --- | --- |
| 4-Deacetoxy-vinblastine (i.p., mice) | >23 |
| Vinblastine (i.p., mice) | 7.5 |
| Vincristine (i.p., mice) | 4.2 |
| N-Formyl-leurosine (i.p., mice) | 29.0 |

Thus the present invention relates to a process for preparing 4-deacetoxy-vinblastine or acid addition salts thereof, having cytostatic properties, wherein an enriched mixture of acid-addition salts of minor diindole alkaloids is treated with a base to liberate the minor diindole alkaloids, the precipitated vinleurosine is separated from the mixture of alkaloid bases, the resulting mother liquor is evaporated, the residue is dissolved in an organic solvent. The resulting solution is extracted with an aqueous phosphate buffer solution of pH 3.7 to 4.3, the separated aqueous-acidic extract is extracted with a chlorinated hydrocarbon, and the chlorinated hydrocarbon phase, containing the major amount of vinblastine, is separated from the aqueous-acidic phase containing the other minor diindole alkaloids. In accordance with the invention one proceeds as follows:

The pH of the aqueous-acidic phase containing the other minor diindole alkaloids obtained in the above step is adjusted with a base to 7.5 to pH=10, preferably pH=9, and the aqueous-alkaline solution is extracted with a chlorinated hydrocarbon. The chlorinated hydrocarbon phase contains N-demethyl-vinblastine, vincristine, minor amounts of vinblastine and 4-deacetoxy-vinblastine and is evaporated. The residue is formylated in a known way to convert all the N-demethylvinblastine to vincristine, the pH of the mixture obtained after formylation is adjusted with a base to pH=7.5 to 10, preferably to pH=8.5 to 9.0, the alkaline solution is extrated with a benzene-type hydrocarbon or with a chlorinated hydrocarbon, the extract is evaporated, the residue, containing 4-deacetoxy-vinblastine, a minor amount of vinblastine and vincristine, is subjected to chromatography on partially deactivated alumina, the separated 4-deacetoxy-vinblastine is optionally converted into an acid addition salt thereof, and, if desired, 4-deacetoxy-vinblastine and/or an acid addition salt thereof is converted into pharmaceutical compositions, such as injectable solutions, tablets, etc., by using conventional pharmaceutical excipients.

In the first step of the process according to the invention the mixture of the acid-addition salts of diindole alkaloids, preferably the mixture of the respective sulfates, is dissolved in an organic solvent. As solvent preferably acetone or a C$_{1-5}$ aliphatic alcohol, particularly methanol is used. The dissolution is performed at a temperature of 0° C. to 50° C., preferably at room temperature.

The solution is treated with a base, such as monoethylamine, diethylamine or pyridine, to liberate the diindole alkaloid bases. The leurosine base separates from the solution at 0° to 25° C. The solution can be cooled to 0° C. in order to achieve a complete separation. The separated leurosine is filtered off, washed with the same solvent used in the dissolution step, and dried. The resulting crude leurosine can be purified, if desired, by known measures, such as by recrystallization. If desired, the leurosine base can be converted into its acid addition salts, preferably into the sulfate.

The mother liquor obtained when separating the leurosine base from the mixture is evaporated under reduced pressure. The residue is dissolved in an organic solvent, preferably in a benzene-type solvent, such as benzene, toluene or xylene. Benzene has proven to be a particularly preferred solvent. In this step the salt (e.g. the sulfate) of the organic base (e.g. monomethylamine, diethylamine, pyridine, etc.), used to liberate the diindole alkaloid bases, separates and can be removed. After the removal of the solids the filtrate is extracted with an aqueous phosphate buffer solution of pH 3.7 to 4.3, preferably of pH 4±0.1. The aqueous-acidic extracts are combined, and the pH of the solution is adjusted with an acid, preferably with phosphoric acid, to 3.5 to 4.1, preferably to 4.0±0.1. The resulting aqueous-acidic solution is extracted with a chlorinated hydrocarbon, preferably with methylene chloride, and the phases are separated. The methylene chloride extracts are combined, dried over sodium sulfate, filtered, and the filtrate is evaporated to dryness under reduced pressure. This operation yields vinblastine as a residue, which can be converted optionally to an acid-addition salt, preferably into the sulfate.

Thereafter the pH of the aqueous-acidic phase is adjusted to 7.5 to pH=10, preferably to 8.5 to 9, by adding a base, preferably aqueous ammonia, to the mixture.

The alkaline solution is extracted with a water-immiscible organic solvent, preferably with a chlorinated hydrocarbon, such as methylene chloride or chloroform. The extracts are combined, evaporated, and the obtained residue which contains vincristine, N-demethyl-vinblastine, a minor amount of vinblastine and 4-deacetoxy-vinblastine is formylated. As formylating agent, preferably, a mixture of formic acid and acetic anhydride is used. Upon this reaction N-demethyl-vinblastine converts quantitatively into vincristine. When the reaction is over the mixture is diluted with a 5 to 15-fold, preferably 10-fold, amount of water and the pH of the diluted solution is adjusted to 7.5 to pH=10, preferably to pH=8.5 to 9.

The alkaline solution is extracted with a water-immiscible organic solvent, preferably with a benzene-type hydrocarbon or a chlorinated hydrocarbon, such as benzene, toluene, xylene, methylene chloride or chloroform. Benzene has proven to be a particularly preferred extracting agent. The extracts are combined and evaporated under reduced pressure. The residue which contains vincristine, a minor amount of vinblastine and 4-deacetoxy-vinblastine is dissolved in an organic solvent or solvent mixture, preferably in a mixture of a benzene-type hydrocarbon and a chlorinated hydrocarbon, particularly in a mixture of benzene and chloroform, and the solution is subjected to column chromatography. As the adsorbent, alumina, particularly partially deactivated alumina is used. The elution is performed preferably with an organic solvent mixture, particularly with mixtures of benzene and chloroform containing the two components in varying amounts. The chromatographic fractions are examined preferably by thin layer chromatography, and the fractions containing the same alkaloid components are combined. The fractions containing vincristine and vinblastine, respectively, are processed according to known techniques, whereas the fractions containing 4-deacetoxy-vinblastine are processed by evaporating to dryness the combined solutions. If desired, the resulting crude 4-deacetoxy-vinblastine can be purified by recrystallization or can be converted into to its acid addition salts.

4-Deacetoxy-vinblastine and/or its acid addition salts can be administered orally and/or parenterally either in single daily dosages or several times a day in subdivided forms. The parenteral route, primarily the intravenous route proved to be a particularly preferred manner of administration.

In order to prepare a parenterally administerable composition the active agent is dissolved in distilled water or physiological saline and/or optionally in an organic solvent, such as in a lower aliphatic alcohol or glycol ether (e.g. ethyleneglycol monoethyl ether). The injectable solutions may contain dissolution aids, such as polyoxyethylene sorbitane derivatives (e.g. Tween 20, Tween 60, Tween 80) and other auxiliary agents, such as preservatives (e.g. benzyl alcohol, p-oxy-benzoic acid esters, etc.), antioxidants (e.g. ascorbic acid, sodium pyrosulfite, tocopherol, etc.), complexing agents (e.g. ethylenediamine tetraacetates), buffers, etc. The pharmaceutical compositions may also contain local anaesthetic agents, such as lidocaine. The solid compositions may contain various carriers, e.g. lactose, etc.

The process of the invention is elucidated in detail by the aid of the following non-limiting Examples.

The physical constants of 4-deacetoxy-vinblastine have been determined as follows: The optical rotation power has been measured on an Opton type polarimeter; whereas the PMR spectra were recorded on a Varian EM 360 type spectrophotometer using deuterochloroform as the solvent and tetramethylsilane as the internal standard.

EXAMPLE 1

Crude 4-deacetoxy-vinblastine 50 g. of a mixture of crude diindole alkaloid sulfates are dissolved in 300 ml. of methanol at room temperature, and 13 ml. of diethylamine are added to the solution with stirring. The solution is maintained at 0° C. for one hour, whereupon the crude leurosine base separates in crystalline form. The crystals are filtered off, washed with a small amount of methanol, and dried in vacuo.

Yield: 6.4 g. of crude leurosine base, which contains 90 to 95% of the leurosine present originally in the starting diindole alkaloid sulfate mixture.

The crude leurosine base is purified by recrystallization. If desired, this compound is converted into its sulfate.

The filtrate obtained when separating the crude leurosine base is evaporated to dryness under reduced pressure, and the residue is dissolved in 2500 ml. of benzene. During this operation diethylamine sulfate separates in crystalline form. The crystals are filtered off, washed with a small amount of benzene, and stored. This salt can be applied for recovering the diethylamine base.

The benzene filtrate is extracted with 3×2500 ml. of an aqueous phosphate buffer solution (pH=4.0±0.1). The phosphate buffer solution is prepared by dissolving 10% by weight of dry sodium dihydrophosphate in water, and adjusting the pH of the solution with 0.1 N phosphoric acid to the above value. The phases formed in the extraction step are allowed to separate, and the aqueous solutions are combined. The pH of the aqueous solution is adjusted to 4.0±0.1 by adding a further amount of 0.1 N phosphoric acid, and then the solution is extracted with 4×2500 ml. of methylene chloride. The methylene chloride phases are combined, dried over sodium sulfate, and evaporated to dryness under reduced pressure.

Yield: 25 g. of vinblastine, which can be used directly, i.e. without any further purification, in the semisynthetic preparation of vincristine.

The obtained 25 g. of vinblastine are dissolved in 80 ml. of methanol, and the solution is acidified to pH=5 with 0.3% by volume ethanolic sulfuric acid. Upon standing, vinblastine sulfate separates in crystalline form.

The pH of the aqueous-acidic phase from the extraction is adjusted to 8.5-9.0 with concentrated aqueous ammonia, and the alkaline solution is extracted with 4×800 ml. of chloroform. The chloroform extracts are combined, dried over sodium sulfate, and filtered. The filtrate is evaporated under reduced pressure, and the residue (8 g of an amorphous alkaloid mixture) is dissolved in a mixture of 45 ml. of formic acid and 11 ml. of acetic anhydride. The solution is allowed to stand at room temperature for 5-15 minutes, and then it is diluted with a ten-fold amount of distilled water cooled previously to 5° C. The pH of the diluted solution is adjusted 8.5-9.0 with concentrated aqueous ammonia, and the alkaline solution is extracted with 4×800 ml. of benzene. The benzene extracts are combined, evaporated under reduced pressure, and the residue (6.9 g. of an amorphous alkaloid mixture) is dissolved in 42 ml. of a 1:1 mixture of benzene and chloroform. The alkaloids are separated from each other by column chromatography. A suspension of 345 g. of alumina (activity grade: IV-V) in a 1:1 mixture of benzene and chloroform is filled into a column with a diameter of 4 cm., and the solution to be treated is poured onto the column.

The alkaloids adsorbed on the column are eluted as follows: elution is started with a 9:1 mixture of benzene and chloroform, and the effluent is collected into fractions of 100 ml. each. The fractions are subjected to thin-layer chromatography (adsorbent: alumina on alumina foil; developing agent: a mixture of 100 ml. of benzene, 50 ml. of chloroform and 7.5 ml. of diethylamine). Fractions Nos. 3 to 10, which contain 4-deacetoxy-vinblastine, are combined and evaporated under reduced pressure. 1.7 g. of crude 4-deacetoxy-vinblastine are obtained.

Fractions Nos. 10 to 36 are eluted with a 4:1 mixture of benzene and chloroform, and the individual fractions are examined by thin-layer chromatography as described above.

Fractions Nos. 11 to 19 are combined and evaporated under reduced pressure. 0.6 g. of an alkaloid mixture are obtained, which contains vinblastine and 4-deacetoxy-vinblastine in an approximate ratio of 1:1. This mixture is subjected to a second chromatographic treatment. The residue is dissolved in a 1:1 mixture of benzene and chloroform, this solution is applied onto a column filled with alumina (activity grade: IV-V), and then the elution is performed as described above. Yield: 0.18 g. of vinblastine and 0.20 g. of 4-deacetoxy-vinblastine.

If desired, this latter chromatographed step can be performed on the combined residues obtained from ten parallel runs.

Fractions Nos. 20 to 24 are combined and evaporated under reduced pressure. 0.9 g of vinblastine are obtained.

Fractions Nos. 25 to 36 contain 0.3 g. of deacetyl-vinblastine.

Fractions Nos. 36 to 45 are eluted with a mixture of benzene and chloroform containing the two components in equal amounts. The effluents are combined and evaporated under reduced pressure. 1.7 g. of vincristine are obtained.

EXAMPLE 2

Purification of 4-deacetoxy-vinblastine 1.7 g. of crude 4-deacetoxy-vinblastine, obtained as described in Example 1, are dissolved in 25 ml. of a 3:2 mixture of methanol and water. The solution is cooled to 5° C. and allowed to stand for 16 hours. The separated crystals are filtered off, washed with 3 to 4 ml. of a 3:2 mixture of methanol and water cooled to 5° C., and dried. 1.3 g. of 4-deacetoxy-vinblastine are obtained; m.p.: 190°-193° C., $\alpha_D^{20} = +107°$ (c=1%, in chloroform).

Analysis: calculated for $C_{44}H_{56}N_4O_7$: C: 70.19%, H: 7.50%, N: 7.44%, O: 14.87%; Found: C: 69.85%, H: 7.52%, N: 7.23%, O: 14.97%.

Mass spectrum

The mass spectrum of 4-deacetoxy-vinblastine was examined in comparison with that of vinblastine. For the deacetoxy compound the molecular ion peak appears at m/e=752, whereas for vinblastine it appears at m/e=810. The difference amounting to 58 mass units is equal to the mass of the acetoxy group.

Both diindole alkaloids consist of a velbamine and a vindoline moieties. Since the mass numbers characteristic of the velbamine fragment and the base peak of the velbamine moiety (m/e=355 and 154) also appear in the mass spectrum of 4-deacetoxy-vinblastine, it follows that the acetoxy group in question is missing from the vindoline fragment. Based on the splitting paths (m/e=122, 135, 224) it is probable that the deacetoxy compound fails to contain the acetoxy group coupled to position 4 of vinblastine.

PMR-spectrum

When comparing the PMR spectrum of 4-deacetoxy-vinblastine with that of vinblastine it appears that the peak observable in the spectrum of vinblastine at $\delta = 2.09$ ppm, which is characteristic of the 4-acetoxy group, cannot be observed in the spectrum of the deacetoxy compound.

The characteristic peaks of the PMR spectrum of 4-deacetoxy-vinblastine are as follows:

$\delta = 2.73$ ppm (N-methyl protons)
$\delta = 3.60$ ppm (carbomethoxy protons)
$\delta = 3.81$ ppm (aromatic —$OCH_3$ protons)
$\delta = 3.85$ ppm (carbomethoxy protons)

EXAMPLE 3

4-Deacetoxy-vinblastine sulfate 1.25% ethanolic sulfuric acid is added to 1.1 g. of crude 4-deacetoxy-vinblastine (prepared as described in Example 1) until the pH of the mixture reaches the value of 4.5. The mixture is allowed to stand at 5° C. for 2 hours. The separated crystals are filtered off and washed with 2 to 3 ml. of 5° C. ethanol. 0.95 g. of crude 4-deacetoxy-vinblastine sulfate are obtained. If desired, this compound can be recrystallized as follows:

0.95 g. of crude 4-deacetoxy-vinblastine sulfate are dissolved in 25 ml. of methanol, and 125 ml. of acetone are added to the solution. The solution is allowed to stand at 5° C. for 2 hours, and the separated crystals are filtered off. The crystals are washed with 2 to 3 ml. of cold acetone, and dried. 0.88 g. of purified 4-deacetoxy-vinblastine sulfate are obtained; $\alpha_D^{20} = +29.0°$ (c=1%, in methanol).

EXAMPLE 4

Pharmaceutical composition containing 4-deacetoxy-vinblastine sulfate

An injectable solution containing 5 ml. per ampule of physiological saline, 50 mg. per ampule of benzyl alcohol, 50 mg. per ampule of lactose and 1, 5 or 7 mg. ampule of freeze-dried 4-deacetoxy-vinblastine sulfate is prepared. The solvent is sterilized by filtration prior to filling it into the ampules.

EXAMPLE 5

Isolation of 4-deacetoxy-vinblastine from the corresponding chromotographic fraction.

The process of Example 1 is followed up to the chromatographic separation of the alkaloid mixture. The fractions 3 to 10, 20 to 24, 25 to 36 and 36 to 45 are worked up as described in Example 1 and the combined fractions 11 to 19 are processed in the following way:

The combined fractions 11 to 19 contain an approximate 1:1 mixture of vinblastine sulfate and 4-deacetoxy-vinblastine sulfate. The combined fractions are evaporated to dryness.

(a) Deacetylation with hydrochloric acid 1 g of the 1:1 mixture of vinblastine sulfate and 4-deacetoxy-vinblastine sulfate obtained as residue of the evaporation of the combined eluate fractions 11 to 19 is dissolved in 20 ml of concentrated hydrochloric acid and the solution is allowed to stand at room temperature. The deacetylation reaction is completed in about 6 hours. The reaction mixture is poured into a double volume of icy water, the pH value is adjusted to between 8.5 and 9 with concentrated ammonium hydroxide solution and this alkaline solution is extracted first with two 20 ml portions and then twice with 10 ml portions of dichloromethane. The combined dichloromethane phases are evaporated to yield 0.7 g of a 1:1 mixture of deacetyl-vinblastine and 4-deacetoxy-vinblastine.

(b) Deacetylation with sodium carbonate (alternative method)

1 g of the 1:1 mixture of vinblastine sulfate and 4-deacetoxy-vinblastine sulfate obtained as residue of the evaporation of the combined eluate fractions 11 to 19 is dissolved in 20 ml of ethanol and 2.5 g of sodium carbonate are added to the solution. The reaction mixture is stirred at room temperature for 3 to 4 hours, the unreacted sodium carbonate is filtered off and washed twice with 5 ml portions of chloroform. The washings are combined with the filtrate, the combined organic solution is washed with 15 ml of water to remove the residual traces of sodium carbonate, then dried with anhydrous sodium sulfate, filtered and the filtrate is evaporated to dryness. 0.7 g of dry residue are obtained, consisting of the 1:1 mixture of deacetyl-vinblastine and 4-deacetoxy-vinblastine. (Potassium carbonate or lithium carbonate may also be used as deacetylating agents.)

(c) Isolation of 4-deacetoxy-vinblastine from the mixture

The 0.7 g of a 1:1 mixture of deacetyl-vinblastine and 4-deacetoxy-vinblastine obtained according to the preceding paragraphs (a) or (b) is dissolved in the 1:1 mixture of benzene and chloroform and the solution is poured onto a chromatographic column containing 30 g of alumina (activity III). The column is eluted with a 1:1 mixture of benzene and chloroform; fractions of 15 ml each are collected.

The fractions 1 to 7 are combined and evaporated to dryness. 0.34 g of 4-deacetoxy-vinblastine are obtained as residue; this product is crystallized as described in Example 2.

The fractions 8 to 14 contain no alkaloids.

The fractions 16 to 19 are combined and evaporated to dryness; 0.29 g deacetyl-vinblastine is obtained as evaporation residue.

(d) Reacetylation of deacetyl-vinblastine 0.29 g of deacetyl-vinblastine is dissolved in 3 ml of acetic anhydride and the solution is allowed to stand for one hour at room temperature. The thus obtained vinblastine is isolated from the reaction mixture in the usual way and then converted into the sulfate salt. 0.28 g of vinblastine sulfate is obtained.

EXAMPLE 6

The initial procedure according to Example 1 is followed to the point where the major portion (25 gm) of the vinblastine is separated from the residue of the minor diindole alkaloids. This residue contains 4-deacetoxy-vinblastine, demethyl-vinblastine, deacetyl-vinblastine and minor amounts of vinblastine and vincristine in an aqueous-acidic phase.

The pH of the aqueous-acidic phase is adjusted to 8.5–9.0 with concentrated ammonia and the aqueous-acidic phase is extracted with 4×800 ml of chloroform. The chloroform extracts are combined, dried and filtered. The solvent is evaporated and the residue is dissolved in a mixture of formic acid and acetic anhydride (4:1). The solution is allowed to stand for 10–15 minutes and is then diluted with about 10 volumes of distilled water cooled to 5° C. The pH is again adjusted to 8.5–9.0 and the solution again extracted with chloroform. The residue after extraction is then subjected to deacetylation either by the procedure of Example 5(a) with acid or Example 5(b) with an alkali carbonate.

Ten grams of the resulting mixture, now containing primarily 4-deacetoxy-vinblastine, deacetyl-vinblastine and vincristine, is dissolved in 50 ml of a 1:1 mixture of benzene and chloroform and the components of the mixture are separated by column chromatography.

The column is prepared by suspending 345 g of alumina (activity grade IV–V) in a 1:1 mixture of benzene and chloroform and filling the suspension into a standard 4 cm chromatography column. The mixture, containing the components, is introduced into this column and the alkaloids are adsorbed therein.

The alkaloids are initially eluted with an eluent of a 9:1 mixture of benzene and chloroform (fractions 1–15). The effluent is collected in 100 ml fractions. (The fractions are followed by thin-layer chromatography using alumina and the developing agent consisting of 100 ml benzene, 50 ml chloroform and 7.5 ml of diethylamine.)

Fractions 1–10 contain the 4-deacetoxy-vinblastine. These fractions are combined and evaporated to dryness. The residue consists of 2.9 g of 4-deacetoxy-vinblastine. This product is recrystallized as described in Example 2.

Fractions 11–15 contain no alkaloids.

Fractions 16–30 are eluted with 4:1 benzene-chloroform eluate.

Fractions 16–30 contain deacetyl-vinblastine. These fractions are combined and evaporated to have a residue of 2.3 g of deacetyl-vinblastine. This product is reacylated according to the procedure of Example 5(d), supra, to yield 2.25 g of vinblastine sulfate.

The residue on the column, if the acid hydrolysis according to Example 5(a) is performed, is N-dimethyl-deacetylvinblastine. The residue is deacetylvincristine if the alkaline hydrolysis procedure according to Example 5(b) is used. These column residues after elution with chloroform are then reconverted to vincristine; the N-dimethyl-deacetylvinblastine is recovered via the usual formylation and acetylation procedures and the deacetylvincristine acetylated in the usual manner.

We claim:

1. A process for separating vinblastine from 4-deacetoxy vinblastine which comprises the steps of:
   (a) subjecting a mixture of diindole alkaloids including vinblastine and 4-deacetoxy vinblastine to deacetylation with a concentrated halo acid or an alkali carbonate to convert the vinblastine in the mixture to deacetyl vinblastine; and
   (b) subjecting the mixture obtained in step (a) to a single chromatographic separation and recovering separately from the single chromatographic separation, a first component containing substantially all of the 4-deacetoxy vinblastine and a second component containing the deacetyl vinblastine
   (c) reacylating said deacetyl vinblastine of said second component with acetic anhydride to convert it to vinblastine.

2. The process defined in claim 1 wherein the deacetylation is carried out with hydrochloric acid or sodium or potassium carbonate.

* * * * *